(12) United States Patent
Mihajlovic et al.

(10) Patent No.: US 8,545,490 B2
(45) Date of Patent: Oct. 1, 2013

(54) APPARATUS, A METHOD AND A COMPUTER PROGRAM FOR APPLYING ENERGY TO AN OBJECT

(75) Inventors: Nenad Mihajlovic, Eindhoven (NL); Joachim Kahlert, Aachen (DE); Ronald Jan Asjes, Eindhoven (NL); Gerardus Everardus Marie Hannen, Eindhoven (NL); Carsten Heinks, Nordhorn (DE); Antonius Johannes Maria Nellissen, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 506 days.

(21) Appl. No.: 12/746,191

(22) PCT Filed: Nov. 26, 2008

(86) PCT No.: PCT/IB2008/054965
§ 371 (c)(1),
(2), (4) Date: Jun. 4, 2010

(87) PCT Pub. No.: WO2009/072035
PCT Pub. Date: Jun. 11, 2009

(65) Prior Publication Data
US 2010/0262130 A1    Oct. 14, 2010

(30) Foreign Application Priority Data

Dec. 6, 2007  (EP) .................................. 07122460

(51) Int. Cl.
*A61B 18/18*    (2006.01)
(52) U.S. Cl.
USPC ........................................................ 606/16

(58) Field of Classification Search
USPC ....................................................... 606/13–16
See application file for complete search history.

(56) References Cited

U.S. PATENT DOCUMENTS

| | | | |
|---|---|---|---|
| 5,366,443 A | 11/1994 | Eggers et al. | |
| 5,578,008 A | 11/1996 | Hara | |
| 5,763,769 A | 6/1998 | Kluzner | |
| 5,871,483 A | 2/1999 | Jackson et al. | |
| 5,991,650 A | 11/1999 | Swanson et al. | |
| 6,425,894 B1 | 7/2002 | Brucker et al. | |
| 7,004,911 B1 | 2/2006 | Tu et al. | |
| 7,171,253 B2 | 1/2007 | Dowlatshahi | |
| 2002/0047002 A1 | 4/2002 | Wheeler | |
| 2002/0107511 A1* | 8/2002 | Collins et al. | 606/41 |

FOREIGN PATENT DOCUMENTS

| | | |
|---|---|---|
| DE | 19734506 A1 | 2/1999 |
| EP | 1642544 A1 | 4/2006 |
| WO | 9510318 A1 | 4/1995 |
| WO | 9600036 A1 | 1/1996 |
| WO | 2006055658 A1 | 5/2006 |
| WO | 2008065609 A1 | 6/2008 |

* cited by examiner

*Primary Examiner* — James Greece (57) ABSTRACT

The present invention relates to an apparatus (1) for applying energy to an object (2), wherein the apparatus (1) comprises an energy emitting element, a temperature sensor and a tube (6), in which the energy emitting element and the temperature sensor are locatable. The energy emitting elements is adapting for applying energy to the object (2) and the temperature sensor is adapted for sensing the temperature of the object (2). Both, the energy emitting element and the temperature sensor can be guided to a location of the object (2), at which the energy is to be applied.

9 Claims, 8 Drawing Sheets

APPARATUS, A METHOD AND A COMPUTER PROGRAM FOR APPLYING ENERGY TO AN OBJECT

CROSS REFERENCE TO RELATED APPLICATIONS

Related applications are PCT/IB2008/054984 (Apparatus, Method and Computer Program for Applying Energy to an Object), filed Nov. 27, 2008 and IB2008/055042 (Apparatus, Method and Computer Program for Applying Energy to an Object), filed Dec. 2, 2008, which are entering the U.S. national stage concurrently with this application.

FIELD OF THE INVENTION

The invention relates to an apparatus, a method and a computer program for applying energy to an object. The invention relates further to a combination element for use in the apparatus for applying energy to an object.

BACKGROUND OF THE INVENTION

An apparatus and a method for applying energy to an object are, for example, used in the field of interventional treatment of atrial fibrillation. During this treatment radio frequency, light or ultrasound energy is applied to the cardiac tissue using a catheter, wherein due to the absorption of the energy in the tissue the myocardium is heated up and the generated thermal energy denaturizes cardiac tissue.

Different catheters have to be placed in the heart chambers at the same time. These catheters are steered and navigated to the heart chambers by either built-in guiding means or by the use of guide wires to guide the catheter passively into the heart. The different catheters are energy application catheters for applying energy for tissue ablation and temperature sensing catheters for sensing the temperature of the heart chamber during the application of energy.

The use of this amount of catheters requires a lot of space and is difficult to handle.

SUMMARY OF THE INVENTION

It is therefore an object of the present invention to provide an apparatus, a method and a computer program for applying energy to an object, wherein the space needed for the energy application and the temperature sensing is reduced and wherein the handling is facilitated. It is a further object of the present invention to provide a corresponding combination element for use in the apparatus for applying energy to an object. In a first aspect of the present invention an apparatus for applying energy to an object is presented, wherein the apparatus comprises:

- an energy emitting element for applying energy to the object,
- a temperature sensor for sensing the temperature of the object,
- a tube, in which the energy emitting element and the temperature sensor are locatable, for guiding the energy emitting element and the temperature sensor to a location of the object, at which the energy is to be applied.

The invention is based on the idea that, since the energy emitting element and the temperature sensor are locatable within the tube, they can together be guided to the location of the object, at which the energy is to be applied. It is not necessary to have one tube containing the energy emitting element for guiding the energy emitting element and another tube containing the temperature sensor for guiding the temperature sensor. Since only one tube is needed for the application of energy and the temperature sensing, the space needed for the application of energy and the temperature sensing is reduced. Furthermore, since only one tube has to be guided, the handling of energy application and temperature sensing is facilitated. The energy emitting element and the temperature sensor can be guided to the location of the object, at which the energy is to be applied, within the tube, and, if this location has been reached, the energy emitting element and the temperature sensor can leave the tube for applying energy to the object and for sensing the temperature of the object.

The apparatus preferentially further comprises guiding means for steering and/or navigating the tube containing the energy emitting element and the temperature sensor to the location, at which the energy has to be applied, in particular within an inner space of an object, like a heart chamber.

The tube is preferentially a catheter, i.e., if the apparatus is used for, for example, an ablation procedure within a heart chamber, only one catheter is needed for ablation and temperature sensing. The tube can comprise several lumina, in which at least the energy emitting element and the temperature sensor are located.

The energy emitting elements can comprise wires and an electrical energy source connected to the wires for applying electrical energy, or optical fibers and an optical energy source, like a laser device, connected to the optical fibers for applying optical energy.

Preferentially, the apparatus comprises a multiple of energy emitting elements for applying energy to the object at different locations and a multiple of temperature sensors for sensing the temperature at the different locations. This allows an application of energy at different locations, in particular simultaneously, and a sensing of the temperature at these locations, in particular simultaneously with the application of energy.

It is further preferred that the apparatus comprises:

- a multiple of energy emitting elements for applying energy to the object at different locations,
- a multiple of temperature sensors for sensing the temperature at the different locations, wherein the energy emitting elements of the multiple of energy emitting elements are individually controllable, wherein the temperature sensors of the multiple of temperature sensors sense the temperature at the different locations independently from each other and wherein each temperature sensor of the multiple of temperature sensors is assigned to an energy emitting element of the multiple of energy emitting elements such that for each location, at which energy is to be applied by an energy emitting element of the multiple of energy emitting elements, the temperature is independently sensable, i.e. measurable.

This allows measuring the temperature of different locations of the object, to which energy is applied, in particular simultaneously with the application of energy, and, thus, the application of energy can be controlled by measuring the temperature at the different locations. Preferentially, the apparatus further comprises a control unit for controlling the application of energy at the different locations in dependence on the sensed temperature at the different locations, preferentially such that the temperature at the different locations does not exceed a predetermined threshold.

In addition to the multiple of energy emitting elements and the multiple of temperature sensors, the apparatus can comprise further energy emitting elements and/or temperature sensors, which are not adapted such that each temperature sensor is assigned to an energy emitting element, i.e., for example, one temperature sensor can also measure the temperature at an intermediate location, which is located between at least two locations, at which energy is to be applied.

It is further preferred that the energy emitting elements are adapted for an ablation procedure applied to tissue of the object, in particular applied to tissue of a human heart.

It is also preferred that the apparatus comprises a multiple of combination elements, wherein each combination element comprises a multiple of energy emitting elements and a multiple of temperature sensors, wherein the energy emitting elements of the multiple of energy emitting elements are wound around a holding element. Since the energy emitting elements are wound around the holding element, the energy emitting elements are arranged close together in a longitudinal direction with respect to the holding element, i.e. with respect to the helix formed by the wound energy emitting elements, leading to a reduced distance between locations, at which energy can be applied, in particular simultaneously.

The holding element is preferentially a wire. It is also preferred that the holding element has a memory-shape effect such that it has a predetermined shape, if it is not in a forced shape, for example, because the holding element is inside the tube, which keeps the holding element in a certain shape, for example, in a linear shape. This allows guiding the energy emitting elements to the locations, at which energy is to be applied, while the combination elements are in a linear shape within the tube, wherein the holding element can give the combination elements a predetermined shape for the application of energy, after the combination element has left the tube at the locations, at which energy is to be applied. The holding element is preferentially a memory metal alloy wire, in particular a nitinol wire.

It is also preferred that the multiple of combination elements form an arrangement, in particular a basket structure, which is changeable between a folded condition, in which the multiple of combination elements are parallel to each other, and an unfolded condition, in which the multiple of combination elements are not parallel to each other, in particular, in which they need more space than in the folded condition and in which the energy emitting elements and the temperature sensors are located on a surface of a volume, in particular a spherical or elliptical volume, defined by the combination elements. This allows guiding the combination elements to the locations, at which energy is to be applied, within the tube, while the combination elements are in the folded condition, wherein, after the locations, at which energy is to be applied, have been reached, the combination elements can leave the tube and can be transformed into the unfolded condition. Preferentially, in the unfolded condition the combination elements are in contact with a surface of the object for applying energy and sensing the temperature.

It is further preferred that the combination element comprises a casing, in which the multiple of energy emitting elements, the multiple of temperature sensors and the holding element are located. The casing is preferentially elastic such that the combination element can be shaped according to the shape of the holding element, in particular if the holding element has a memory effect. The casing is preferentially made of a bio-compatible material. It is further preferred that the casing is adapted such the energy emitting elements are coupled to the object for applying energy and that the temperature sensors are thermally coupled to the object. If the energy emitting elements apply, for example, optical energy and if they comprise optical fibers, the optical fibers are wound around the holding element and the casing is at least partly optically transparent. In particular, the casing comprises an optical window, which preferentially also allows passing thermal energy, i.e. which is preferentially thermally conductive. In addition, the cladding and a possible further coating of the optical fibers are removed at the locations, at which the optical energy should leave the combination element, in particular at the window within the casing. Preferentially micro-lenses for focusing and/or steering light can be added to the window. It is further preferred that the window comprises spreading particles that preferentially do not absorb light, like $TiO_2$. It is also preferred that the optically transparent window is electrically non-conductive in order to not transmit an electrical signal from the object, which could be the heart. It is further preferred that the window is large enough in the longitudinal direction for allowing applying energy by each optical fiber through the optically transparent window to the object. The window can also comprise at least two kind of materials, an optically transparent material and a thermally conductive material, wherein the optically transparent material is located at locations, at which the optical energy should leave the casing, and wherein the thermally conductive material is located at locations, at which the temperature sensors are located.

In a preferred embodiment, at least one of the temperature sensors is a thermocouple comprising at least a first metal element and a second metal element, which comprise different types of metal and which are contacted to each other. The metal elements are, for example, wires, metallic foils and/or metallic coatings. By using such a thermocouple the temperature at the contacts between the first and second metal element can easily be measured by measuring the voltage between the first and second metal elements. At locations not being the contact location the first and second metal elements are insulated from each other by insulation means like insulation layers.

It is further preferred that the energy emitting element comprises an optical fiber and that the first metal element and/or the second metal element are a metal coating on the optical fiber. This allows a larger degree of integration of the temperature sensor and the energy emitting element.

It is also preferred that the first and/or second metal elements are wound around the holding element together with the energy emitting elements. This further integrates the temperature sensors and energy emitting elements leading to a reduction of space needed for the energy emitting elements and the temperature sensors and a reduction of the distance between the energy emitting elements and the temperature sensors, wherein the temperature at a location, at which energy is to be applied, can be determined with an improved accuracy.

The holding element is preferentially metallic, wherein the holding element is preferentially one of the first and second metal elements. Since the holding element has preferentially two functions, holding of elements and being part of a temperature sensor, the degree of integration is further improved. The holding element can be metallic, for example, because it is a metallic wire and/or because it comprises a metallic coating, wherein the metallic coating preferentially serves as at least one of the first and second metal elements.

It is further preferred that the first and the second metal elements are coatings on an element of the apparatus. In particular, the coatings forming the first and second elements are located on the same element of the apparatus. In this embodiment, further metallic elements like wires are not needed by the temperature sensors, thereby further reducing the space needed for the temperature sensors. The element of the apparatus, on which the coatings are present, is, for example, an optical fiber or the holding element. The coating forming the first metal element and the coating forming the second element are preferentially in contact at one location, at which the temperature should be measured, and are separated from each other by an insulating layer at other locations.

In a further preferred embodiment, different thermocouples have the identical first or second metal element. This further increases the degree of integration.

In a further aspect of the present invention a combination element for use in the apparatus as defined in claim 1 is presented, wherein the combination element comprises a multiple of energy emitting elements and a multiple of temperature sensors and wherein the energy emitting elements of the multiple of energy emitting elements are wound around a holding element.

In a further aspect of the present invention a method for applying energy to an object is presented, wherein the method comprises following steps:

guiding the energy emitting element and the temperature sensor to a location of the object, at which the energy is to be applied, by using a tube, in which the energy emitting element and the temperature sensor are located, applying energy to the object using the energy emitting element, sensing the temperature of the object using the temperature sensor.

In a further aspect of the present invention a computer program for applying energy to an object is presented, wherein the computer program comprises program code means for causing a computer to carry out the steps of the method as defined in claim 11, when the computer program is run on a computer controlling an apparatus as defined in claim 1.

It shall be understood that the apparatus of claim 1, the combination element of claim 10, the method of claim 11 and the computer program of claim 12 have similar and/or identical preferred embodiments, in particular as defined in the dependent claims.

It shall be understood that preferred embodiments of the invention can also be any combination of the dependent claims with the respective independent claim.

BRIEF DESCRIPTION OF THE DRAWINGS

These and other aspects of the invention will be apparent from and elucidated with reference to the embodiments described hereinafter. In the following drawings

DETAILED DESCRIPTION OF EMBODIMENTS

Figure 1:
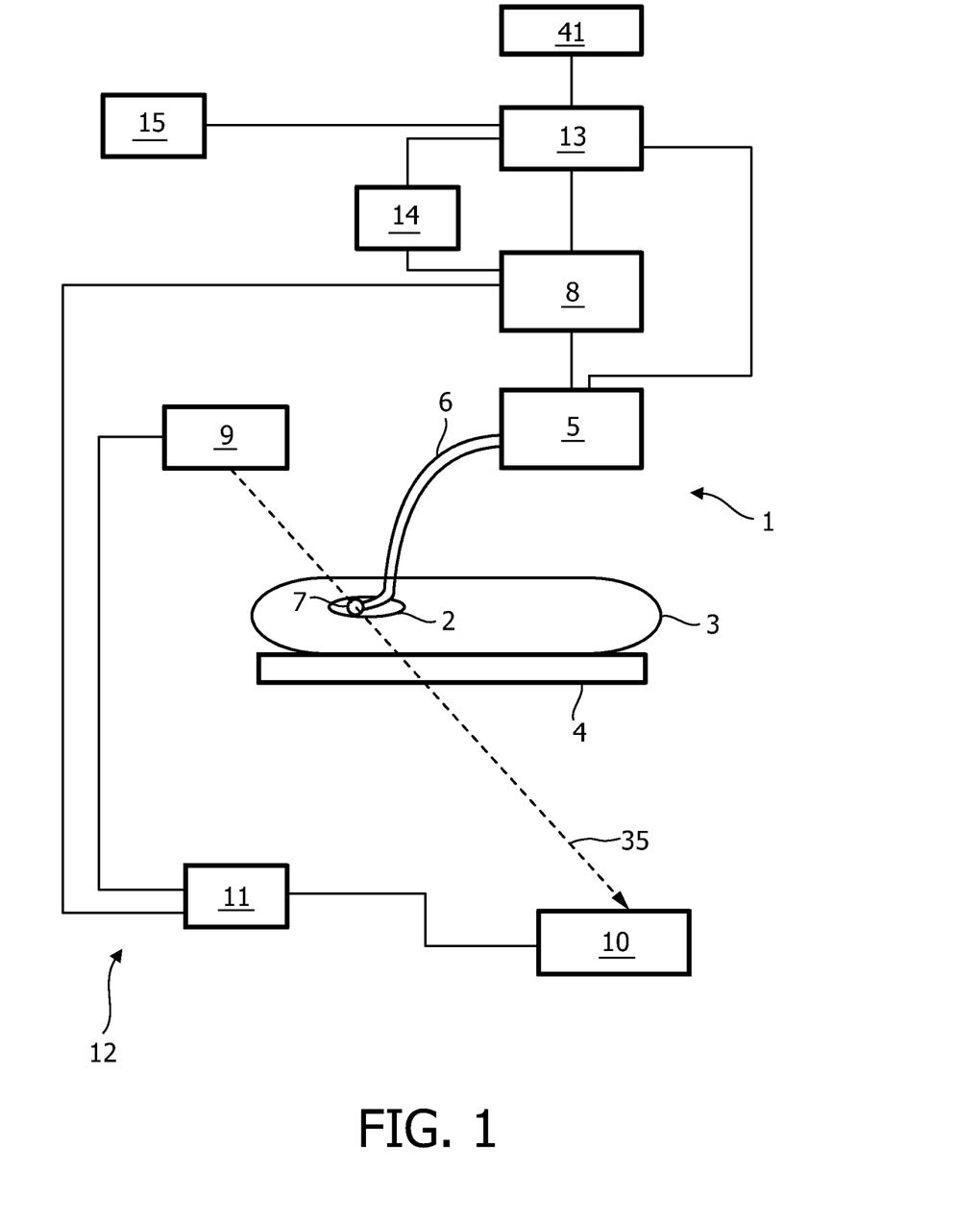
FIG. 1 shows schematically and exemplarily an embodiment of an apparatus for applying energy to an object in accordance with the invention.

FIG. 1 shows an apparatus 1 for applying energy to an object. The apparatus 1 comprises a tube, in this embodiment a catheter 6, and an arrangement 7 of energy emitting elements and temperature sensors. The arrangement 7 of energy emitting elements and temperature sensors is connected to a control unit 5 via the catheter 6. The catheter 6 with the arrangement 7 of energy emitting elements can be introduced into an object 2, which is, in this embodiment, a heart of a patient 3 located on a patient table 4, wherein the catheter 6 is steered and navigated to the heart chambers by built-in guiding means (not shown). In another embodiment, the catheter can, for example, be steered and navigated by the use of an introducer to guide the catheter passively into the heart.

During introduction of the arrangement 7 and the catheter 6 into the object 2 an imaging device 12, which is in this embodiment a fluoroscopy device, generates images of the object 2 and the arrangement 7. This imaging device 12 preferentially generates images of the object 2 and the arrangement 7, also if the arrangement 7 is already located within the object 2.

In other embodiments, the object can, for example, be another hollow organ of a patient or a technical object, in particular, a hollow technical object, whose inner surface has to be treated with energy.

The imaging device 12, i.e. in this embodiment the fluoroscopy device 12, comprises an X-ray source 9 and a detection unit 10, which are controlled by a fluoroscopy control unit 11. The fluoroscopy device 12 generates X-ray projection images of the object 2 and of the arrangement 7 in a known way. The X-rays of the X-ray source 9 are schematically indicated by the arrow 35.

In another embodiment, instead of a fluoroscopy device, another imaging device can be used for generating an image comprising the object 2 and the arrangement 7. For example, a magnetic resonance imaging device, an ultra sonic imaging device or a computed tomography imaging device can be used for generating an image of the object 2 and the arrangement 7.

Figure 2:
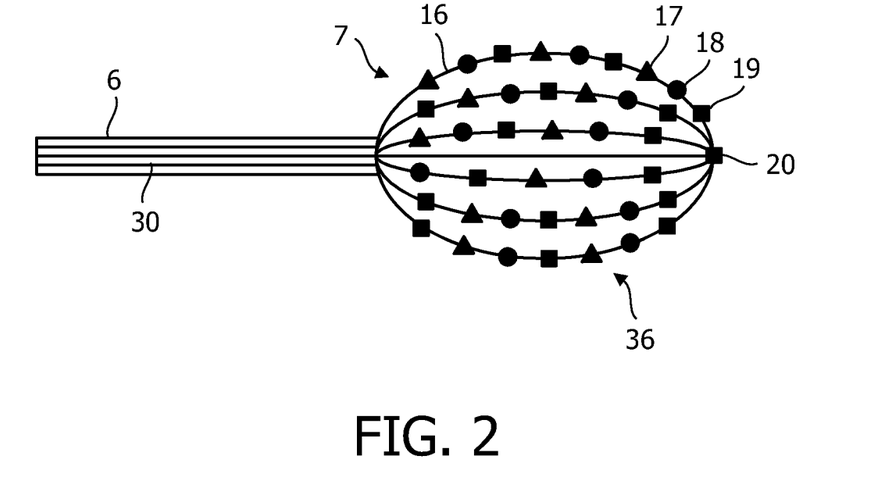
FIG. 2 shows schematically and exemplarily an arrangement of energy emitting elements and temperature sensors in an unfolded condition.

An embodiment of an arrangement 7 and a catheter 6 is schematically shown in more detail in FIG. 2. The arrangement 7 is changeable between an unfolded condition, in which emission locations 19 of the energy emitting elements and temperature sensing locations 17 of the temperature sensors of the arrangement 7 are located on an abutting surface 36 for abutting against a surface of the object, and an folded condition, in which the arrangement 7 takes a smaller space, which allows to introduce the arrangement 7 into the object 2. In FIG. 2 the arrangement 7 is shown in its unfolded condition. The arrangement 7 comprises a basket made of several splines being combination elements 16 comprising emission locations 19 of the energy emitting elements (indicated by squares) and the temperature sensing locations 17 of the temperature sensors (indicated by triangles). The distribution of the emission locations 19 of the energy emitting elements and the temperature sensing locations 17 of the temperature sensors 17 in FIG. 2 is only schematically and exemplarily and does not limit the invention to a certain distribution. Preferentially, to each emission location 19 of the energy emitting elements a temperature sensing location 17 of a temperature sensor is assigned, which is located as close as possible to the corresponding emission location 19 of the energy emitting elements, in order to measure the temperature at the location, at which the energy is applied to the object. In this embodiment, the arrangement 7 comprises further sensing elements 18 (indicated by circles), for example, for electrical sensing. In other embodiments, the further sensing elements 18 can be omitted.

Preferentially, the emission locations 19 of the energy emitting elements are evenly distributed along the combination elements 16 and along the abutting surface 36.

In the unfolded condition, which is shown in FIG. 2, the combination elements 16 of the arrangement 7 form substantially an ellipsoid or sphere. Thus, in the unfolded condition, the abutting surface 36 is preferentially a surface of an ellipsoid or sphere. For applying energy to the object 2, the abutting surface 36 preferentially abuts against a surface of the object 2 such that the positions of the emission locations 19 of the energy emitting elements, of the temperature sensing locations 17 of the temperature sensors and of possible further sensing elements 18 remain unchanged relative to the surface of the object 2 during the application of energy to the object 2 and during sensing the surface of the object 2. This fixed positions of the emission locations 19 of the energy emitting elements and of temperature sensing locations 17 of the temperature sensors and of possible further sensing elements 18 relative to the object surface are preferentially achieved by elastics properties of the combination elements 16 and, therefore, of the arrangement 7. This elasticity of the combination elements 16 results in an elastic force, which presses the emission locations 19 of the energy emitting elements, the temperature sensing locations 17 of the temperature sensors and possible further sensing elements 18 against the object surface. The elasticity of the combination elements 16 also allows conforming of the abutting surface 36 to the object surfaces and following a motion of the object 2, while the emission locations 19 of the energy emitting elements and the sensing elements 17, 18 are continuously in contact with the object surface, or, in other embodiments, the distance between the emission locations 19 of the energy emitting elements and the sensing elements to the object surface remains continuously constant, even if the object 2 moves.

Figure 3:
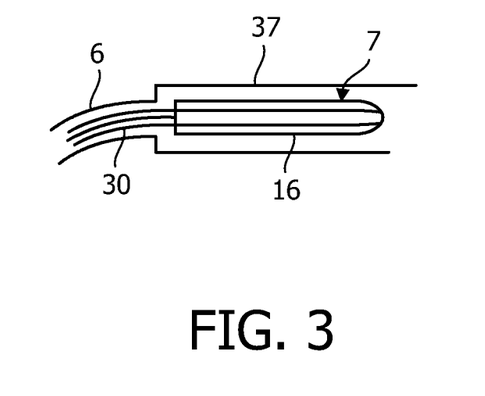
FIG. 3 shows schematically and exemplarily the arrangement of energy emitting elements and temperature sensors in a folded condition.

The combination elements 16 comprise holding elements, which are preferentially wires made of a memory alloy. In this embodiment the holding elements are made of nitinol. For unfolding the arrangement 7, i.e. for unfolding of the basket, the memory effect of the nitinol is used. The nitinol wires are pre-shaped and elastic as a spring. In the folded condition, which is schematically shown in FIG. 3 and in which the arrangement 7 takes a smaller space, the combination elements 16 of the arrangement 7 are located within a catheter shaft 37, in particular, in a small pipe within the catheter shaft 37. For unfolding the arrangement 7, i.e. for changing from the folded condition to the unfolded condition, the combination elements 16 are moved out of the catheter shaft 37, wherein the arrangement 7 forms the abutting surface 36 because of the memory effect of the nitinol wires.

FIG. 3 is a schematic view only. In order to enhance the clarity of the folded condition, the illustration shows only some combination elements of the arrangement 7 and no emission locations of the energy emitting elements and temperature sensors, although they are still present.

In an embodiment, on the distal part of the abutting surface 36 an emission location 20 of an energy emitting element is located, i.e. the emission location 20 of the energy emitting element is located on the tip of the arrangement 7. This allows applying energy to certain locations of the object 2, if the combination elements 16 are at least almost completely located within the catheter shaft 37, wherein only a small part of the combination elements 16, i.e. at least only the emission location 20 of the energy emitting element, is located outside of the catheter shaft 37. Thus, energy can be applied to a certain location of the object 2, even if the arrangement 7 is in the folded condition.

The emission locations 19, 20 of the energy emitting elements are connected to one or several energy sources via lines 30 such that at least some of the emission locations 19, 20 of the energy emitting elements can apply energy to the object 2 independently from each other. It is preferred that the emission locations 19, 20 of the energy emitting elements are connected to one or several energy sources via the lines 30 such that each emission location 19, 20 of the energy emitting elements can be addressed separately, i.e. that each emission location 19, 20 of the energy emitting elements can apply energy to the object independently from a possible application of energy caused by the other emission locations 19, 20 of the energy emitting elements.

At the emission locations at the optical fibers 30 the cladding and possible further coatings have been removed such that optical energy can leave the optical fiber and be applied to the object. These emission locations are connected via the lines 30, which are in this embodiment the optical fibers, to one or several light sources, which are preferentially lasers. In this embodiment, each emission location 19 is connected to one or several separate laser devices via the optical fiber 30 to address each emission location 19 separately. In other embodiments, in addition or alternatively, the emitting energy elements can be electrodes for applying electrical energy.

The emission locations 19 can be connected to one or several laser devices such that, after the laser beams of the laser devices have been divided, for example by beam splitters, each emission location is connected to an individual laser beam, wherein the intensity of each individual laser beam can be modified, in order to address each emission location 19 separately. Alternatively, each emission location 19 can be connected to an individual laser device such that to each emission location 19 one of several laser devices is assigned.

The optical fibers 30 of the energy emitting elements are wound around the nitinol wire of the corresponding combination element 16.

Each combination element 16 comprises an elastic casing, which is made of a bio-compatible material. A part of a combination element 16, which such an elastic casing 38, is schematically shown in FIG. 4.

Figure 4:
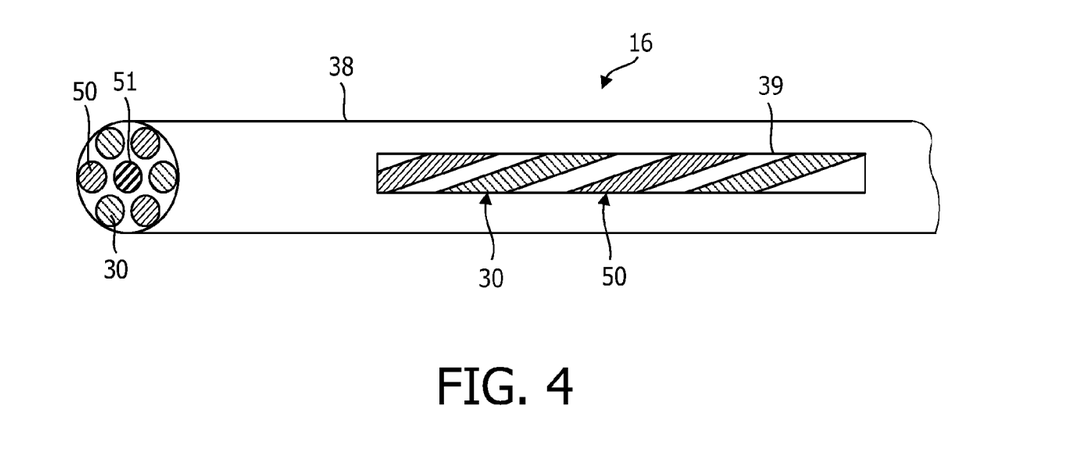
FIG. 4 shows schematically and exemplarily a combination element.

In FIG. 4, several optical fibers 30 are wound around the holding element 51. In addition, several wires 50 being part of the temperature sensors are wound around the holding element 51. The wires 50 have preferentially the same or a similar diameter as the fibers 30. The optical fibers 30 and the wires 50 wound together around the holding element 51 are located within the elastic casing 38. The casing 38 comprises a window 39, through which light can leave the casing 38. The window 39 should be long enough to be able to access each fiber 30 and wire 51 (each fiber and each wire will preferentially be accessed only once). In order to have a thermocouple, being in this embodiment the temperature sensor, a galvanic contact between each wire 50 and the holding element 51 being in this embodiment a nitinol wire is made. In other embodiments, the nitinol wire can be coated with an appropriated metal coating, wherein each wire has a galvanic contact with the metal coating for forming a thermocouple.

At the energy emission locations 19 a cladding of the optical fibers 30 and possible further coatings of the optical fibers 30 are removed, in order to allow light leaving the optical fibers 30. This is schematically and exemplarily shown in FIG. 5.

Figure 5:
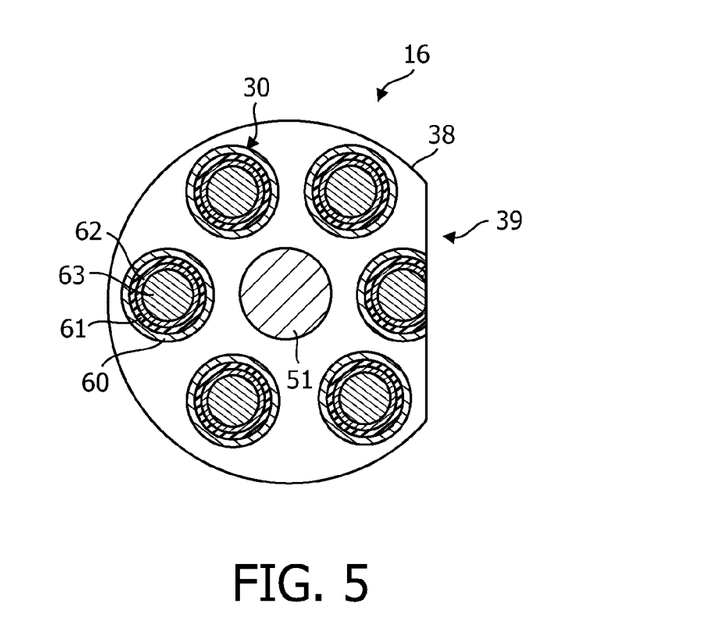
FIG. 5 shows schematically and exemplarily a sectional view through a combination element.

FIG. 5 shows schematically and exemplarily a sectional view through the combination element 16, wherein at the window 39 at a location, at which light should leave a fiber core 63 of the optical fiber 30 and transmit through the window 39, the cladding 62 and possible further coatings, in particular, an electrically insulating material 60 and a conductive coating 61 are removed, in particular, by grinding.

The combination element can comprise a single window or several windows in the casing, which allow a transmission of optical and thermal energy and, if, for example, also electrical sensing elements are present within the casing, of electrical energy. In other embodiments, the energy emission locations 19 and the temperature sensing locations 17 and possible further sensing elements 18 are not distributed over the whole arrangement 7, as schematically and exemplarily shown in FIG. 2, but only within a part of the combination elements constituting the arrangement.

Figure 6:
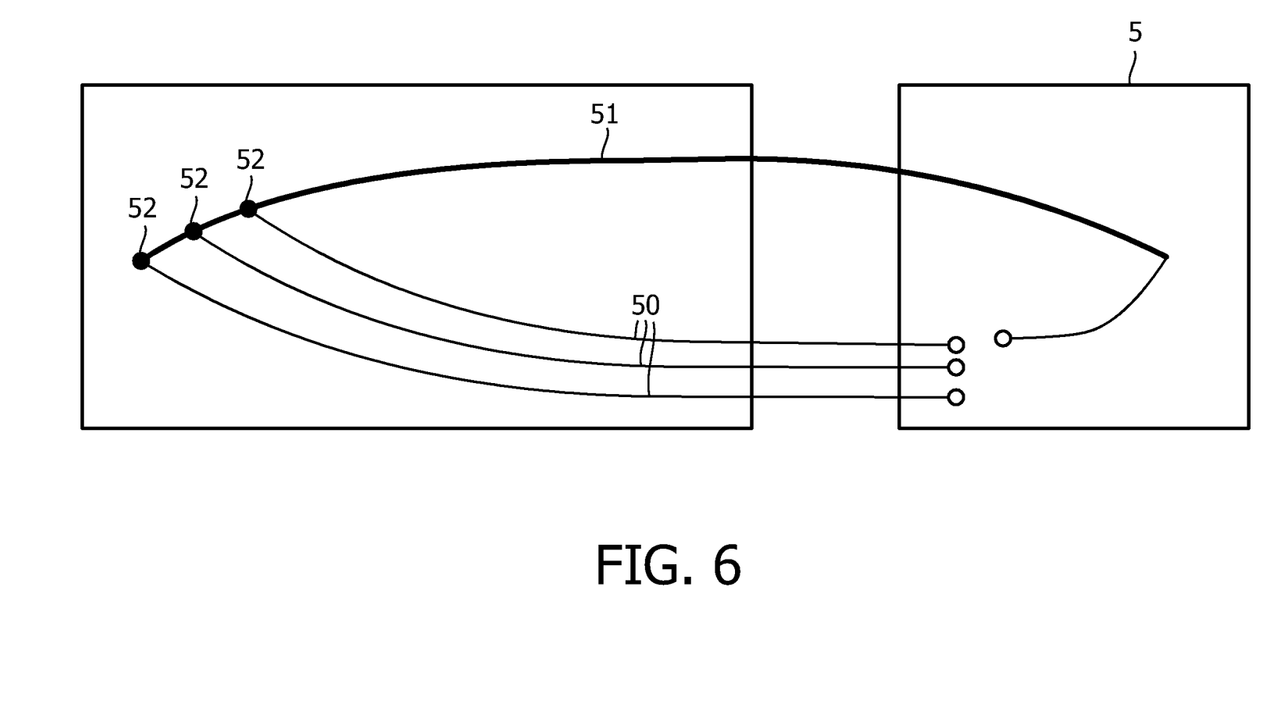
FIG. 6 shows schematically and exemplarily a construction of temperature sensors.

Every contact between a wire 50 and the nitinol wire 51, or in another embodiment every contact between a wire 50 and a metal coating on the nitinol wire, forms a temperature sensing location of a temperature sensor. The schematic representation of the wires 50 which are connected to one common mode wire 51, or the coating of the common mode wire, for forming thermocouples is shown in FIG. 6. In FIG. 6, three thermocouples are made by contacting the three wires 50 at the different temperature sensing locations 52 to the holding element 51 within a combination element 6. In the control unit 5 the voltage between a wire 50 and the holding element 51 is measured for determining the temperature at the temperature sensing location 52. In another embodiment, instead of or in addition to the nitinol wire a nitinol tube can be used. The nitinol tube can, for example, be used for pumping a liquid like a saline solution through the lumen for, for example, irrigation or cooling.

The window 39 of the casing 38 is preferentially thermally conductive and optically transparent to light. The window 39 is preferentially adapted such that it supports light spreading. In other embodiments, the window can comprise at least two different materials, one thermally conductive placed close to the temperature sensing locations and one optically transparent placed close to the energy emission locations. The two different materials can be arranged alternately in the longitudinal direction.

Figure 7:
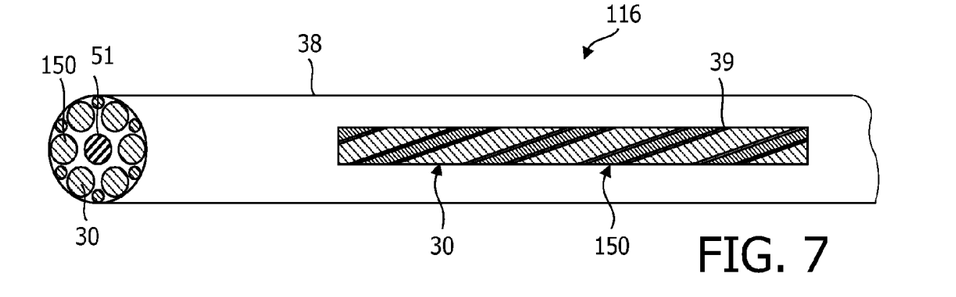
FIGS. 7 to 10 show schematically and exemplarily further combination elements.

FIG. 7 shows exemplarily and schematically a further embodiment of a combination element 116. Similar elements in FIG. 4 and FIG. 7 are indicated by similar reference signs. The combination element 116 shown in FIG. 7 differs from the combination element 16 in the diameter of the wires 150 with respect to the diameter of the optical fibers 30. In the embodiment shown in FIG. 7 the diameter of the wires 150 is smaller than the diameter of the optical fibers 30. This allows increasing the number of energy emitting elements and temperature sensors locatable within the casing 38. A casing is preferentially made by coating a bundle of energy emitting elements and temperature sensors.

A nitinol wire has preferentially a diameter smaller than 200 μm, further preferred smaller than 150 μm, further preferred smaller than 100 μm and has preferentially a diameter of 50 or 100 μm. The electrical wires have preferentially a diameter smaller than 100 μm, further preferred smaller than 50 μm, and have preferentially a diameter of 20 μm. The diameter of a single fiber is preferentially smaller than 300 μm, preferentially 250 μm, further preferred smaller than 200 μm, preferentially 125 μm, further preferred smaller than 100 μm, preferentially 60 μm. The diameter of a fiber can also be 3 μm, in particular, when manufactured in a bundle.

Figure 8:
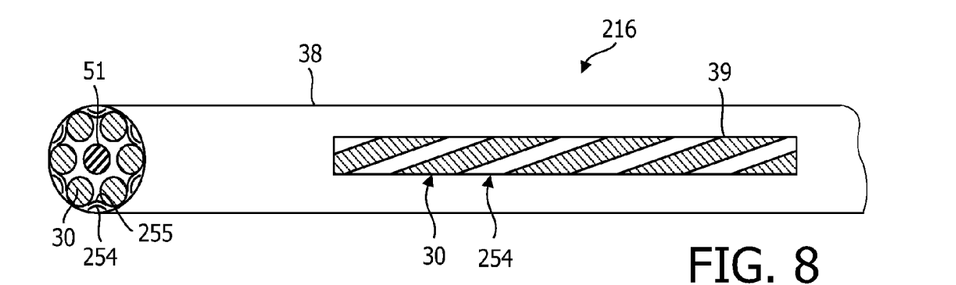

In the above described embodiments the wires 50, 150 are a first metal element of a thermocouple and the holding element 51 or a metal coating on the holding element 51 serves as a second metal element of a thermocouple. In FIG. 8, a combination element 216 is exemplarily and schematically shown, in which two metallic foils form first and second metal elements of a thermocouple. Similar elements in FIGS. 4, 7 and 8 are indicated by similar reference signs.

Instead of wires 50, 150 two metal foils 254, 255 are wounded around the holding element 51. As every first and second metal element of a thermocouple used in this description, the two metal foils 254, 255 are insulted one with respect to another and are connected at a single point, which forms the temperature sensing location. The insulation between the first and second metal elements is not shown in the figures for clarity reasons.

By using foils multi track connection/thermocouples can be made by lithographic processes. The foil thickness can be as thin as 25 μm with a 0.5 . . . 5 μm thick metal layer.

Figure 9:
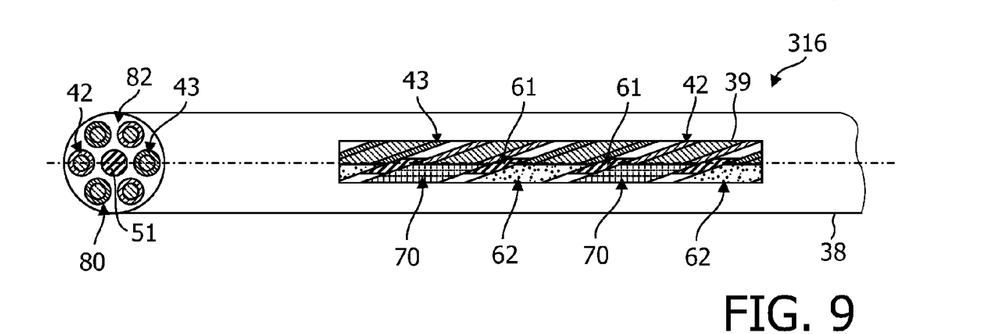

A further embodiment of a combination element 316 is schematically and exemplarily shown in FIG. 9. Again, similar elements in FIGS. 4, 7, 8 and 9 are indicated by similar reference signs.

The combination element 316 comprises optical fibers 80, 82, which comprise a metal coating 42, 43. At the location of the window 39 a galvanic contact is made between the metal coating 43 and the holding element 51 or between the metal coating 43 and a metal coating on the holding element 51 at temperature sensing locations 33 for forming a thermocouple. At electrical sensing locations 70 electrical signals of the object are received using the metal coatings 42 of the optical fibers 82. An irrigation opening to the tubular holding element 51 is arranged at the irrigation locations 61. The temperature sensing locations 62 are located close to the energy emission locations, at which light leaves the optical fibers.

Figure 10:
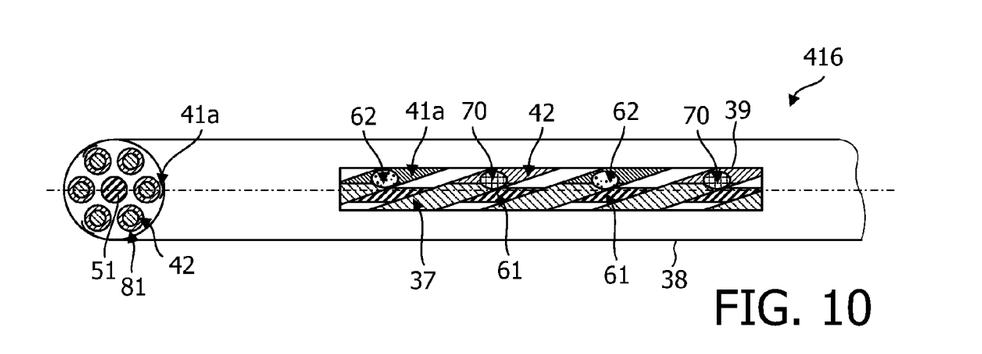

FIG. 10 shows schematically and exemplarily a further embodiment 416 of a combination element. The combination element 416 comprises several optical fibers 81 as energy applying elements, which are coated with a metal coating 42. As a sensing element or a part of a sensing element to at least some of the optical fibers 81, in particular, to each of the optical fibers, a metallic foil 41a is added, wherein the metal coating 42 is electrically insulated with respect to the metallic foil 41a. At the temperature sensing locations 62 a galvanic contact is made between the metallic foil 41a and the metal coating 42. The galvanic contacts generate thermocouples for measuring the temperature. In another embodiment at the temperature sensing locations a thermocouple is created by coating each or at least some of the optical fibers with at least two metal coatings with an electrical insulation coating layer between them. At the temperature sensing locations a galvanic contact is made between the two metal coating layers for making the thermocouple. Furthermore, a metal coating on an optical fiber or on a holding element can be used for forming an electrical conductor for sensing electrical potentials of the object, in particular, in a human heart. In the embodiment 416 shown in FIG. 10, irrigation openings 61 are present in the tubular holding element 51 for irrigating the location, at which the optical energy is applied, in particular, for irrigation lesion locations.

Electrical sensing locations, temperature sensing locations and/or irrigation locations are also arranged in the windows of the combination elements shown in FIGS. 4, 7 and 8 and are not shown for clarity reasons.

In FIGS. 4, 7 to 10, certain numbers of energy emitting elements and temperature sensors are shown, but in other embodiments also other numbers of energy emitting elements and temperature sensors can be present. Furthermore, additional sensing elements can be present, for example, for electrical sensing, even if they are not shown in the figures.

The casing 38 preferentially comprises an optically transparent window 39, which is located at the energy emission locations for allowing the energy to leave the casing 38. Alternatively, a casing can be used, which is completely optically transparent.

The sensing elements are preferentially used for monitoring the temperature and possible further properties of the object, like the electrical potential, during the application of the energy.

In the above mentioned embodiments, the temperature sensors are thermocouples. In other embodiments, other temperature sensors can be used, for example, the temperature can be measured optically.

Since these temperature measurements do not interfere with the application of optical energy by the energy emitting elements, the sensing of the object 2 and the application of energy can be performed simultaneously. This allows monitoring the properties of the objects, in particular, of the object surface, while energy is applied to the object. For example, if energy is applied for performing an ablation procedure, the progress of this procedure can be monitored during the ablation procedure.

In another embodiment, a time-multiplex method can be used, which alternately applies energy and senses the temperature of the object.

The sensor elements can also comprise spectroscopic sensors for sensing light backscattered and/or reflected from the object. The backscattered and/or reflected light is transmitted to a spectroscope via an optical fiber for a spectroscopic examination of the object.

The sensing elements are individually addressable. For example, electrical sensors, like electrical potential sensors or temperature sensors, are individually contacted by wires and optical sensors are individually contacted via optical fibers. This means, each sensing location is preferentially contacted via a separate line.

The combination elements shown in FIGS. 4, 7 to 10 are shown such that the left side of the combination elements is open. The left open side is only shown for illustrating the arrangement of elements within the optical fiber and within the combination elements, but, in real, the left sides shown in FIGS. 4, 7 to 10 are closed such that preferentially all light energy is reflected, and is also coated with an electrical insulating material. The right hand side shown in FIGS. 4, 7 to 10 is preferentially connected, in particular, plugged in, to an optical device and an electrical device for applying and/or sensing energy.

The casing shown in FIGS. 4, 7 to 10 can be a coating. Furthermore, the energy applying elements and preferentially also sensing elements can be directly wound around the holding element, preferentially if they comprise an outer insulating coating or if they are not electrically conductive, or with a distance to the holding element. In the latter case, spacers can be arranged in between or the casing can comprise lumina, which are generally separated from each other and in which the energy application element and preferred sensing elements are located, and which are in connection, where required for forming energy emission and/or sensing locations.

Figure 11:
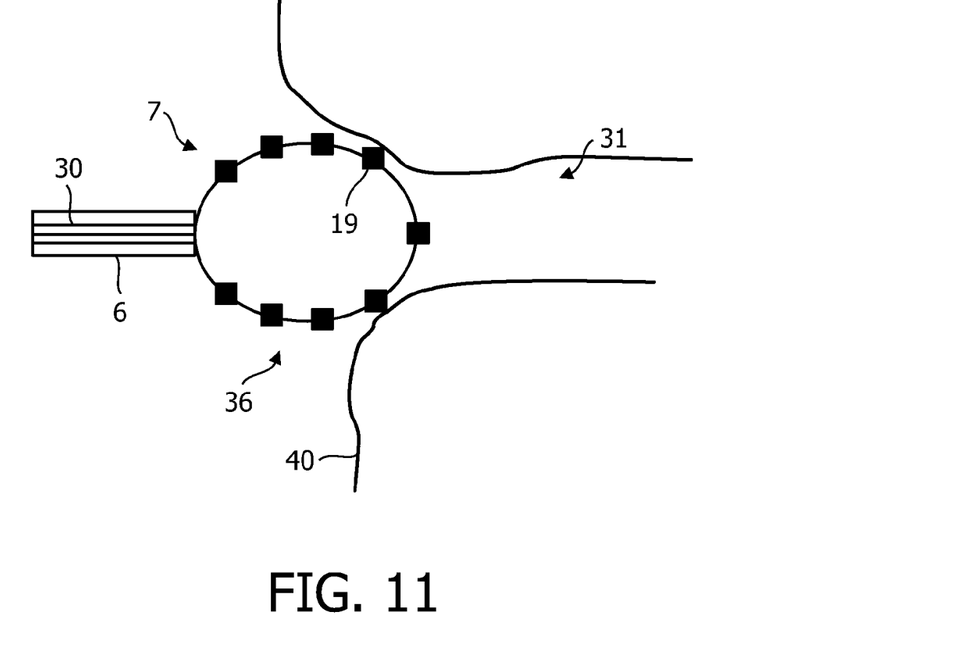
FIG. 11 shows schematically and exemplarily the arrangement of energy emitting elements and temperature sensors in contact with a surface of an object.

FIG. 11 shows schematically an arrangement 7 located within a heart of a patient in an unfolded condition, in which the abutting surface 36 abuts against the object surface 40 around an ostium of a pulmonary vein 31, i.e. in this embodiment a part of the abutting surface 36 abuts against the object surface 40. Energy emitting elements can apply energy via the energy emission locations 19, in this embodiment light energy, to the object surface 40 independently from each other and, in particular, via energy emitting elements 19 being in contact with the object surface 40, in order to denaturize heart tissue around the ostium or the pulmonary vein 31.

FIG. 11 shows schematically only two combination elements of the arrangement 7 without a casing and without temperature sensors for illustration purposes. Nevertheless, also in the situation shown in FIG. 11, the arrangement 7 comprises several combination elements, wherein each combination element includes several energy emitting elements and temperature sensors enclosed within a casing, as described above and, for example, schematically shown in FIGS. 4 and 7 to 10.

Figure 12:
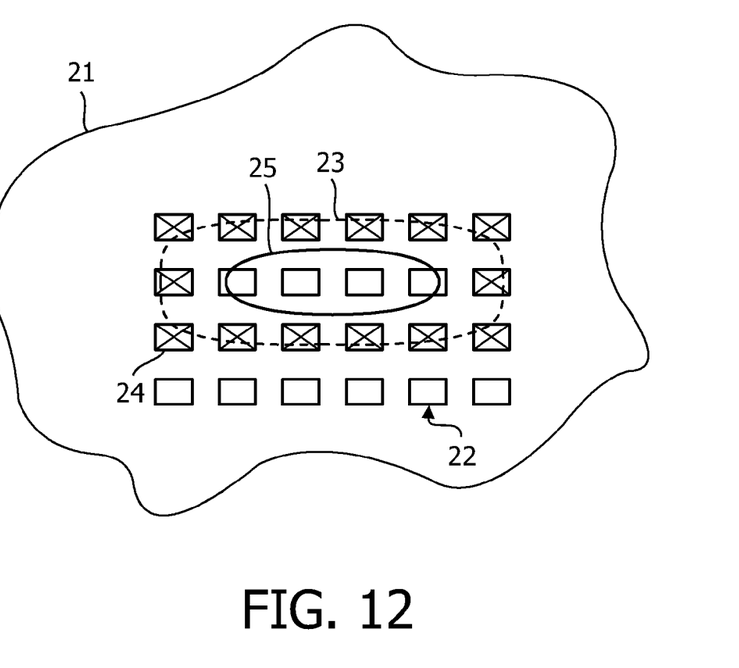
FIG. 12 shows schematically and exemplarily a model of an abutting surface of the arrangement of energy emitting elements and temperature sensors located on a three-dimensional model of the object.

In this embodiment, the apparatus 1 for applying energy to an object is provided with a three-dimensional model of the object 2. This three-dimensional model can, for example, be generated by generating an image of the object 2 by an imaging device, like a computed tomography device, a magnetic resonance imaging device or a ultrasonic imaging device, by segmenting the object 2 and, for example, rendering of the segmented object 2. Furthermore, the apparatus 1 for applying energy to an object is further provided with a model of the abutting surface 36, which comprises, in this embodiment, the dimensions and the positions of the energy emitting elements 19, 20 on the abutting surface 36. A three-dimensional model 21 of the object 2 and a model 22 of the abutting surface 36 are schematically shown in FIG. 12.

The model 22 of the abutting surface 36 is registered with the three-dimensional model 21 of the object by using the image generated by the fluoroscopy device 12. This registration is performed by a registration unit 8 of the apparatus 1.

The registration unit 8 is adapted for registering the three-dimensional model 21 of the object 2 with respect to the image generated by the imaging device 12, which is, in this embodiment, a two-dimensional projection image. For registering of the three-dimensional model of the object of the two-dimensional projection image known 2D-3D-registration methods can be used.

Furthermore, the registration unit 8 is adapted for registering the model 22 of the abutting surface 36 with respect to the image generated by the imaging device 12. Also for this registration, known 2D-3D-registration methods can be used. Since both models 21, 22 have been registered with respect to the two-dimensional projection image, these two models 21, 22 are registered with respect to each other.

The apparatus 1 for applying energy to an object further comprises a visualization device, which is, in this embodiment, a monitor 13, the visualization device is adapted for showing the three-dimensional model 21 of the object 2 and the model 22 of the abutting surface 36. The apparatus 1 for applying energy to an object further comprises an input device 15, like a mouse or a keyboard to allow a user to draw a path 23 on the three-dimensional model 21 of the object, along which energy should be applied to the object 2. Based on this path 23 an energy emitting element determination unit 41 determines energy emitting elements of the model 22 of the abutting surface 36 which are located on or as close as possible to this path 23. In FIG. 12 these determined energy emitting elements 24 are shown with crosses.

In the example shown in FIG. 12, the three-dimensional model 21 is a three-dimensional model of a heart showing an ostium 25 of a pulmonary vein. The heart tissue around the ostium 25 should be denaturized. Therefore, a user has inputted a path 23, which surrounds the ostium 25 of the pulmonary vein. The energy emitting elements 24, which are shown with a cross, are located on or close to the path 23, and during a following ablation procedure energy will be applied to the object 2 via the crossed energy emitting elements 24.

Other paths, along which energy should be applied to the object, can be provided in accordance with the invention. For example, for a linear ablation procedure, an open path, which is substantially linear and which connects two ostia of pulmonary veins, can be used for applying energy along this path.

The energy emitting elements 24 are determined such that energy is applied to the object in a spatially continuous way, i.e. that energy is applied continuously along the respective path, without having gaps, at which energy has not been applied. Referring again to FIG. 1, optionally, the apparatus 1 for applying energy to an object further comprises a path determination unit 14, which automatically determines the path 23 on the three-dimensional model 21 of the object. In this case, the path determination unit 14 receives the three-dimensional model 21 of the object and/or sensing values of the sensing elements for determining the properties of the object, and the path determination unit 14 determines a path 23 from the model 21 and/or the determined properties of the object depending on the desired treatment of the object. For example, if the object is a heart and the path has to encircle the ostium of a pulmonary vein, which can be determined from the model 21 and/or the sensing values, for example, from an electrical potential image of the heart generated by using sensing electrodes, the path is determined such that it encloses, with a given distance to the edge of the ostium, the ostium of the pulmonary vein. The given distance can be predetermined by a user like a physician. The determined path is shown on the visualization device 13.

The input device 15 is adapted such that a user can modify the path 23 and/or at an additional path on the three-dimensional model 21 of the object. Furthermore, the input device 15 is adapted for modifying the determined emitting elements 24, which should apply energy. Furthermore, the apparatus 1 for applying energy to an object can be adapted for allowing a user to select the energy emitting elements 24, which should apply energy, directly with or without showing a path 23.

Figure 13:
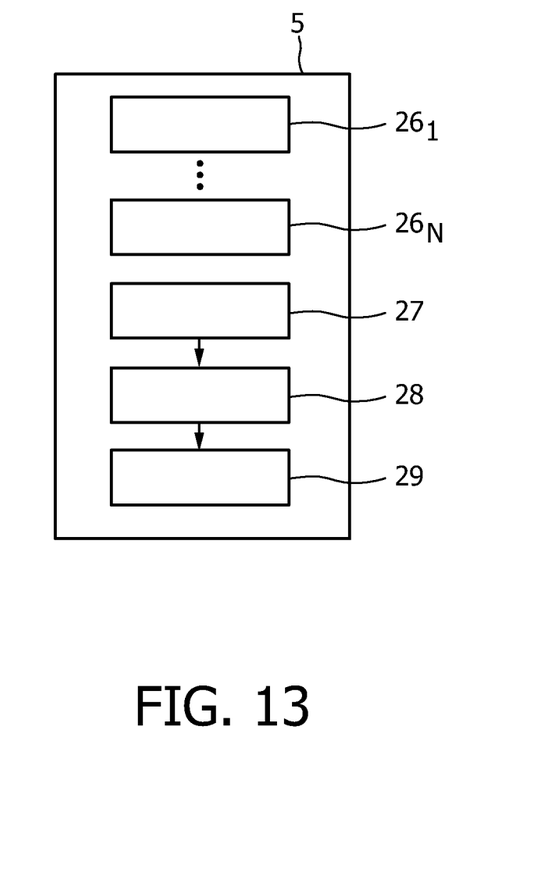
FIG. 13 shows schematically and exemplarily a control unit of the apparatus for applying energy to an object and FIG. 14 shows a flow chart illustrating a method for applying energy to an object in accordance with the invention.

FIG. 13 shows schematically the control unit 5 of the apparatus 1 for applying energy to an object. In this embodiment, the control unit 5 comprises several light sources, in particular, laser devices $26_1 \ldots 26_N$, wherein the number N of these laser devices corresponds to the number of the separate optical fibers 30 of the energy emitting elements of the arrangement 7. Each laser device $26_1 \ldots 26_N$ is coupled to a separate energy emitting element. The control unit 5 further comprises a property determination 27, which receives temperature values from the temperature sensors from the temperature sensing locations 17. If the apparatus comprises further kinds of sensing elements, the property determination unit 27 can receive further kinds of sensing values from the additional sensing elements. The property determination unit 27 determines from these sensing values properties of the object 2, at least the temperature, and, if additionally an electrical sensing is performed, the electrical potential. These properties are transmitted to a deviation determination unit 28, which determines, whether the determined properties are within a given range of operation. If the determined properties are not within a given range of operation, an alarm signal unit 29 outputs an acoustical or an optical signal indicating that the determined properties are out of range. Preferentially, the control unit 5 automatically reduces the intensity of the energy applied to the object, in particular, stops the application of energy, if the deviation determination unit 28 determines that at least one determined property of the object is out of range.

Although, the above described arrangement 7 has been shown in FIG. 11 and in FIG. 12 as covering one ostium of a pulmonary vein, the ablation surface can also be dimensioned such that it can cover two ostia of pulmonary veins.

Figure 14:
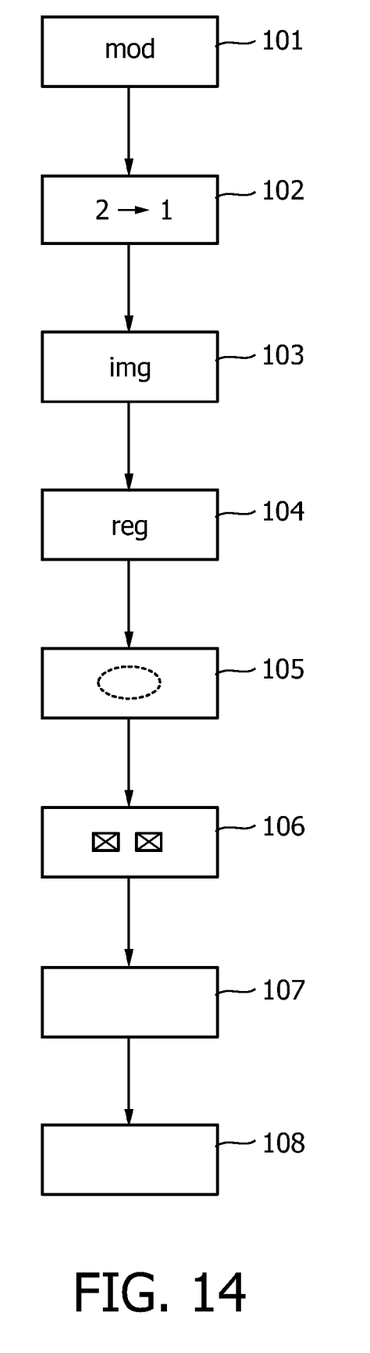

In the following a method for applying energy to an object in accordance with the invention will be described in more detail with reference to a flowchart shown in FIG. 14.

In step 101 a three-dimensional model 21 of the object 2 is provided to the apparatus 1 for applying energy to an object. Furthermore, a model 22 of the abutting surface 36 is provided to the apparatus 1 for applying energy to an object.

In step 102 the arrangement 7 of energy emitting elements, which have been guided into the object 2, is unfolded, in order to transfer the arrangement 7 of energy emitting elements from the folded condition to the unfolded condition in which the abutting surface 36 abuts against an inner surface of the object 2 preferentially such that the position of the energy emitting elements with respect to the inner object surface remains constant during the following procedures.

In step 103 the imaging device 12 generates an image of the object 2 and of the abutting surface 36, and this image is transferred to the registration unit 8.

The three-dimensional model 21 of the object 2 and the model 22 of the abutting surface 36 are registered relative to each other by using the image of the image generation device 12.

The registered models 21, 22 are visualized on the visualization device 13, and a path on the three-dimensional model 21 of the object 2 can be inputted to the apparatus 1 for applying energy to an object via the input device 15. As a default, the path determination unit 14 can determined a default path, which is also visualized on the visualization device 13 and which can be modified by a user using the input device 15.

Energy emission locations 24 of energy emitting elements are determined in step 106, which are located on the given path or are located close to the given path, in order to map the given path to the abutting surface 36 as good as possible, by the energy emitting element determination unit 41. The position of these energy emission locations, which should apply energy to the object, can be modified by a user via the input device 15.

In step 107 energy is applied to the object by the energy emitting elements comprising the energy emission locations, which have been determined and possibly modified by a user in step 106. While applying energy to the object, the properties of the object are monitored by the temperature sensors and possible further sensing elements, the property determination unit 27 and the deviation determination unit 28.

The application of the energy is stopped in step 108, if a user inputs a corresponding stop signal into the apparatus 1 for applying energy to an object by the input device 15, if the property determination unit 27 determines properties of the object, which correspond to predetermined properties, which indicate the wanted modification of the object, or if the deviation determination unit 28 determines that at least one of the properties of the object are out of range, in particular, if the temperature is out of range, i.e. exceeds are predefined threshold value.

The described method using the apparatus 1 for applying energy to an object allows positioning the arrangement 7 of energy emitting elements roughly relative to the object, because the exact path, along which energy has to be applied to the object, is not determined by the positioning of the ablation surface 36, but by the determination and possibly modification of the energy emission locations in step 106. Therefore, a time consuming positioning of the energy emitting elements can be omitted.

The three-dimensional model of the object, in particular, of a heart can be a purely anatomical model or an electro-anatomical model using the electrical potentials measured by the sensing electrodes.

The energy of the energy emitting elements can be applied concurrently or automatically in time coordinated way. Furthermore, the successful application of energy, in particular, the successful ablation can be validated by the measuring the temperature of the object. Since the energy emission locations and the temperature sensing locations are located close to each other, the temperature at the locations, at which energy is applied, can be monitored with high accuracy.

If electrical sensing elements are present for measuring the electrical potential, an electro-anatomical mapping of the object can be provided, in particular of the heart tissue, which can be used for detecting relevant structures like the ostium of the pulmonary veins. This electro-anatomical mapping can also be used to determine a model of the object and to register the model of the object with a model of the abutting surface of the arrangement of emitting elements.

In step 107 the energy applied to the object can be controlled such that too high temperatures in the object, in particular, in the heart tissue, are avoided. Thus, if the temperature becomes too high, the control unit 5 reduces preferentially the energy applied to the object. In the case of heart tissue, a temperature above 80° C. is generally too high.

The invention can be used, for example, be used for ablation in four chambers of a heart, for an electrical isolation of pulmonary veins and for a substrate modification.

The light sources $26_1 \ldots 26_N$ are preferentially infrared laser devices with a wavelength in the range of 960 nm to 1100 nm.

Furthermore, the position of a structure of interest, for example of the ostium of the pulmonary vein, can be located by sensing the electrical potentials at the object surface by electrical sensing elements. The location of the structure of interest can be mapped into a geometrical map, and this geometrical information of the location and the size of the ostium of a pulmonary vein can be mapped into a three-dimensional model of the object, in particular, of a heart of a patient. The size and the position of the ostium will be shown on the three-dimensional model of the object by the visualization device 13 for allowing a user to input a path, along which energy has to be applied, or allow automatically determining such a path.

Although, a fluoroscopy device has been described above as the imaging device, another imaging device, for example, a magnetic resonance device or an ultrasonic imaging device can be used in order to visualize the object and the arrangement of energy emitting elements particularly in real time.

The apparatus 1 for applying energy to an object can be used, for example, for circumferential ablation linear, and/or segmental ablation and/or a single point ablation.

In particular, a computer program for applying energy to an object can comprise program code means for causing a computer to control the application of energy to the object by the energy emitting element of the apparatus as defined in claim 1 in dependence on sensed temperature sensed by the temperature sensor of the apparatus.

While the invention has been illustrated and described in detail in the drawings and foregoing description such illustration and description are to be considered illustrative or exemplarily and not restrictive. The invention is not limited to the disclosed embodiments. Other variations to the disclosed embodiments can be understood and effected by those skilled in the art and practicing the claimed invention, from a study of the drawings, the disclosure, and the appended claims.

In the claims the word "comprising" does not exclude other elements or steps and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the internet or other wired or wireless telecommunication systems.

Any reference signs in the claims should not be construed as limiting the scope of the invention.

The invention claimed is:

1. An apparatus for applying energy to an object, the apparatus comprising:
   an energy emitting element for applying energy to the object,
   a temperature sensor for sensing the temperature of the object,
   a tube, in which the energy emitting element and the temperature sensor are locatable, for guiding the energy emitting element and the temperature sensor to a location of the object, at which the energy is to be applied, wherein
   the energy emitting element comprises an optical fiber, and
   the temperature sensor is a thermocouple comprising at least a first metal element and a second metal element, which comprise different types of metal and which are contacted to each other, at least one of the first metal element and the second metal element are a metal coating on the optical fiber.

2. The apparatus as defined in claim 1, the apparatus comprising:
   a plurality of energy emitting elements for applying energy to the object at different locations,
   a plurality of temperature sensors for sensing the temperature at the different locations,
   wherein the energy emitting elements of the plurality of energy emitting elements are individually controllable, wherein the temperature sensors of the plurality of temperature sensors sense the temperature at the different locations independently from each other and wherein each temperature sensor of the plurality of temperature sensors is assigned to an energy emitting element of the plurality of energy emitting elements such that for each location, at which energy is to be applied by an energy emitting element of the plurality of energy emitting elements, the temperature is independently sensable.

3. The apparatus as defined in claim 1, wherein the apparatus comprises a plurality of combination elements, wherein each combination element comprises a plurality of energy emitting elements and a plurality of temperature sensors, wherein the energy emitting elements of the plurality of energy emitting elements are wound around a holding element.

4. The apparatus as defined in claim 3, wherein at least one of the temperature sensors is a thermocouple comprising at least a first metal element and a second metal element, which comprise different types of metal and which are contacted to each other and wherein at least one of the first and the second metal elements are wound around the holding element together with the energy emitting elements.

5. The apparatus as defined in claim 3, wherein at least one of the temperature sensors is a thermocouple comprising at least a first metal element and a second metal element, which comprise different types of metal and which are contacted to each other and wherein the holding element is metallic and wherein the holding element is one of the first and second metal elements.

6. The apparatus as defined in claim 3, wherein different thermocouples have the identical first or second metal element.

7. A combination element for use in the apparatus as defined in claim 1, wherein the combination element comprises a plurality of energy emitting elements and a plurality of temperature sensors and wherein the energy emitting elements of the plurality of energy emitting elements are wound around a holding element.

8. A method for applying energy to an object, the method comprising following steps:
   guiding the energy emitting element and the temperature sensor to a location of the object, at which the energy is to be applied, by using a tube, in which the energy emitting element and the temperature sensor are located,
   applying energy to the object using the energy emitting element, wherein
   the energy emitting element comprises an optical fiber,
   sensing the temperature of the object using the temperature sensor wherein the temperature sensor is a thermocouple comprising at least a first metal element and a second metal element, which comprise different types of metal and which are contacted to each other, at least one of the first metal element and the second metal element are a metal coating on the optical fiber.

9. A computer program product for applying energy to an object, the computer program product comprising a non-transitory computer-readable storage medium having encoded thereon computer program code for causing a computer to carry out the steps of the method as defined in claim 8, when the computer program code is run on a computer controlling an apparatus for applying energy to an object, the apparatus comprising:
   an energy emitting element for applying energy to the object,
   a temperature sensor for sensing the temperature of the object,
   a tube, in which the energy emitting element and the temperature sensor are locatable, for guiding the energy emitting element and the temperature sensor to a location of the object, at which the energy is to be applied, wherein the energy emitting element comprises an optical fiber, and
   the temperature sensor is a thermocouple comprising at least a first metal element and a second metal element, which comprise different types of metal and which are contacted to each other, at least one of the first metal element and the second metal element are a metal coating on the optical fiber.

* * * * *